(12) United States Patent
Juraszyk et al.

(10) Patent No.: US 6,946,489 B2
(45) Date of Patent: Sep. 20, 2005

(54) SUBSTITUTED BIPHENYL DERIVATIVES

(75) Inventors: Horst Juraszyk, Seeheim (DE); Dieter Dorsch, Ober-Ramstadt (DE); Werner Mederski, Zwingenberg (DE); Christos Tsaklakidis, Weinheim (DE); Christopher Bames, Bad Soden (DE); Johannes Gleitz, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 264 days.

(21) Appl. No.: 10/239,397

(22) PCT Filed: Mar. 23, 2001

(86) PCT No.: PCT/EP01/03375

§ 371 (c)(1),
(2), (4) Date: Jan. 14, 2003

(87) PCT Pub. No.: WO01/70678

PCT Pub. Date: Sep. 27, 2001

(65) Prior Publication Data

US 2004/0220241 A1 Nov. 4, 2004

(30) Foreign Application Priority Data

Mar. 24, 2000 (DE) .......................................... 100 14 645

(51) Int. Cl.⁷ ...................... A61K 31/165; C07C 233/00
(52) U.S. Cl. ....................................... 514/619; 564/164
(58) Field of Search ........................... 514/619; 564/164

(56) References Cited

U.S. PATENT DOCUMENTS 5,962,695 A    10/1999  Nagahara et al.
6,545,055 B1 *  4/2003  Zhu et al. .................... 514/613
6,638,980 B1 * 10/2003  Su et al. ...................... 514/620

FOREIGN PATENT DOCUMENTS

| EP | 0540051 | 5/1993 |
|----|---------|--------|
| EP | 1078917 | 2/2001 |
| WO | WO 9941231 | 8/1999 |
| WO | WO 0071512 | 11/2000 |

* cited by examiner

*Primary Examiner*—Deborah C. Lambkin
(74) *Attorney, Agent, or Firm*—Millen, White, Zelano & Branigan, P.C.

(57) ABSTRACT

The invention relates to compounds of the formula I

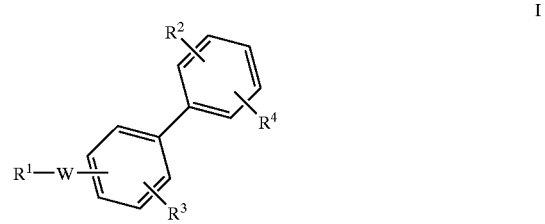

in which $R^1$, $R^2$, $R^3$, $R^4$ and X have the meaning indicated in the text. The compounds act as inhibitors of factors Xa and VIIa and can therefore be employed for the control and prevention of thromboembolic conditions such as thrombosis, myocardial infarct, arteriosclerosis, inflammation, apoplexy, angina pectoris, restenosis after angioplasty and intermittent claudication.

19 Claims, No Drawings

SUBSTITUTED BIPHENYL DERIVATIVES

The invention relates to compounds of the formula I

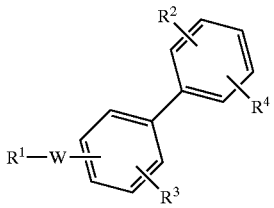

in which:

R¹ is: phenyl or naphthyl, which is substituted by —C(=NH)NH₂, that can also be monosubstituted by —COA, —CO—[C(R⁷)₂]ₙ-Ar', —COOA, —OR⁷, —OCOA, —OCO—[C(R⁷)₂]ₙ-Ar' or by a conventional amino protective group, —NHC(=NH)—NH₂, —CON=C(NH₂)₂,

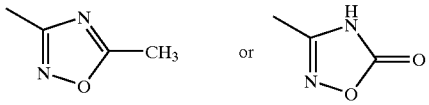

and which can optionally be substituted by -A, —OR⁵, —N(R⁵)₂, —NO₂, —CN, -Hal, —NR⁵COA, —NR⁵COAr', —NR⁵SO₂A, —NR⁵SO₂Ar', —COOR⁵, —CON(R⁵)₂, —COR⁷, —COAr' or S(O)ₙA;

R² is: —S(O)ₙA, —CF₃, —COOR⁷, —OA;

R³, R⁴ are: independently of one another —H, -A, —OR⁵, —N(R⁵)₂, —NO₂, —CN, -Hal, —NR⁵COA, —NR⁵COAr', —NR⁵SO₂A, —NR⁵SO₂Ar', —COOR⁵, —CON(R⁵)₂, —CONR⁵Ar', —COR⁷, —COAr', —S(O)ₙA;

R⁵, R⁶ are: independently of one another —H, -A, —[C(R⁷R⁸)]ₙAr' or —[C(R⁷R⁸)]ₙHet;

R⁷, R⁸ are: independently of one another —H or -A;

W is: —[C(R⁵R⁶)]mCONR5[C(R⁵R⁶)]ₗ—, —OC(R⁵R⁶)ₘCONR⁵[C(R⁵R⁶)]ₗ—;

A is: alkyl having 1 to 20 C atoms, in which one or two CH₂ groups can be replaced by O or S atoms or by —CH=CH— groups and also 1 to 7 H atoms can be replaced by —F;

Ar is: phenyl or naphthyl, unsubstituted or mono-, di- or trisubstituted by -A, -Ar'-, -Het, —OR⁵, —N(R⁵)₂, —NO₂, —CN, -Hal, —NR⁵COA, —NR⁵COAr, —NR⁵SO₂A, —NR⁵SO₂Ar', —COOR⁵, —CON(R⁵)₂, —CONR⁵Ar', —COR⁷, —COAr', —SO₂NR⁵, —S(O)ₙAr' or —S(O)ₙA;

Ar' is: phenyl or naphthyl, unsubstituted or mono-, di- or trisubstituted by -A, —OR⁷, —N(R⁷)₂, —NO₂, —CN, -Hal, —NR⁷COA, —NR⁷SO₂A, —COOR⁷, —CON(R⁷)₂, —COR⁷, —SO₂NR⁷ or —S(O)ₙA;

Het is: a mono- or binuclear saturated, unsaturated or aromatic heterocycle having 1 to 4 N, O and/or S atoms, bonded via N or C, which can be unsubstituted or mono-, di- or trisubstituted by -A, —OR⁷, —N(R⁷)₂, —NO₂, —CN, -Hal, —NR⁷COA, —NR⁷SO₂A, —COOR⁷, —CON(R⁷)₂, —COR⁷, —SO₂NR⁷, —S(O)ₙA and/or carbonyl oxygen;

Hal is: —F, —Cl, —Br or —I;

l is: 0 or 1;

m is: 1, 2 or 3;

n is: 0, 1 or 2;

and their pharmaceutically tolerable salts and solvates.

The invention also relates to the optically active forms, the racemates, the diastereomers and the hydrates and solvates, e.g. alcoholates, of these compounds.

The invention is based on the object of discovering novel compounds having valuable properties, in particular those which can be used for the preparation of medicaments.

It has been found that the compounds of the formula I and their salts have very valuable pharmacological properties together with good tolerability. In particular, they show factor Xa-inhibiting properties and can therefore be employed for the control and prevention of thromboembolic conditions such as thrombosis, myocardial infarct, arteriosclerosis, inflammation, apoplexy, angina pectoris, restenosis after angioplasty and intermittent claudication.

The compounds of the formula I according to the invention can furthermore be inhibitors of the clotting factors factor VIIa, factor IXa and thrombin of the blood-clotting cascade.

Compounds which act as inhibitors on factor Xa are described, for example, in EP 540 051, WO 96/10022, WO 97/08165, WO 96/40679 and WO 98/28282. The antithrombotic and anticoagulant effect of the compounds according to the invention is attributed to the inhibitory action against the activated clotting protease, known under the name factor Xa, or to the inhibition of other activated serine proteases such as factor VIIa, factor IXa or thrombin.

Factor Xa is one of the proteases which is involved in the complex process of blood clotting. Factor Xa catalyses the conversion of prothrombin into thrombin. Thrombin cleaves fibrinogen into fibrin monomers, which contribute elementarily to thrombus formation after crosslinkage. Activation of thrombin can lead to the occurrence of thromboembolic conditions. Inhibition of thrombin, however, can inhibit the fibrin formation involved in thrombus formation.

Measurement of the inhibition of thrombin can be carried out, for example, according to the method of G. F. Cousins et al. in *Circulation* 1996, 94,1705–1712.

Inhibition of factor Xa can thus prevent thrombin being formed.

The compounds of the formula I according to the invention and their salts intervene by inhibition of factor Xa in the blood-clotting process and thus inhibit the formation of thrombi.

The inhibition of factor Xa by the compounds according to the invention and the measurement of the anticoagulant and antithrombotic activity can be determined according to customary in vitro or in vivo methods. A suitable process is described, for example, by J. Hauptmann et al. in *Thrombosis and Haemostasis* 1990, 63, 220–223.

The measurement of the inhibition of factor Xa can be carried out, for example, according to the method of T. Hara et al. in *Thromb. Haemostas.* 1994, 71, 314–319. After binding to tissue factor, the clotting factor VIIa initiates the extrinsic part of the clotting cascade and contributes to the activation of factor X to factor Xa. Inhibition of factor VIIa thus prevents the formation of factor Xa and thus subsequent thrombin formation.

The inhibition of factor VIIa by the compounds according to the invention and the measurement of the antocoagulant and antithrombotic activity can be determined by customary in vitro or in vivo methods. Customary procedure for measurement of the inhibition of factor VIIa is described, for example, by H. F. Ronning et al. in *Thrombosis Research* 1996, 84, 73–81.

The clotting factor IXa is generated in the intrinsic clotting cascade and is likewise involved in the activation of factor X to factor Xa. Inhibition of factor IXa can therefore prevent factor Xa being formed, in a different way.

The inhibition of factor IXa by the compounds according to the invention and the measurement of the anticoagulant and antithrombotic activity can be carried out by customary in vitro or in vivo methods. A suitable procedure is described, for example, by J. Chang et al. in *Journal of Biological Chemistry* 1998, 273, 12089–12094.

The compounds of the formula I can be employed as pharmaceutically active compounds in human and veterinary medicine, in particular for the control and prevention of thromboembolic conditions such as thrombosis, myocardial infarct, arteriosclerosis, inflammation, apoplexy, angina pectoris, restenosis after angioplasty and intermittent claudication.

The following compounds are of particular importance:

2-(3-carbamimidoylphenoxy)-N-(2'-methanesulfonylbiphenyl-4-yl)acetamide (1),
2-(3-carbamimidoylphenoxy)-N-(2'-methanesulfonylbiphenyl-4-yl)butyramide (2),
2-(3-carbamimidoylphenoxy)pentanoic acid (2'-methanesulfonylbiphenyl-4-yl)amide (3),
(S)-2-(3-carbamimidoylphenoxy)pentanoic acid (2'-methanesulfonylbiphenyl-4-yl)amide (4),
(R)-2-(3-carbamimidoylphenoxy)pentanoic acid (2'-methanesulfonylbiphenyl-4-yl)amide (5),
(2-(3-carbamimidoylphenoxy)pentanoic acid (2'-ethanesulfonylbiphenyl-4-yl)amide (6),
(2-(3-carbamimidoylphenoxy)hexanoic acid (2'-methanesulfonylbiphenyl-4-yl)amide (7),
(2-(3-carbamimidoylphenoxy)heptanoic acid (2'-methanesulfonylbiphenyl-4-yl)amide (8),
2-(3-carbamimidoylphenoxy)-N-(2'-methanesulfonylbiphenyl-4-yl)-3-methylbutyramide (9),
2-(3-carbamimidoylphenoxy)-4-methylpentanoic acid (2'-methanesulfonylbiphenyl-4-yl)amide (10),
2-(3-carbamimidoylphenoxy)-4-methylpentanoic acid (2'-methanesulfonylbiphenyl-4-yl)amide (11),
2-(3-carbamimidoylphenoxy)-N-(2'-ethanesulfonylbiphenyl-4-yl)-2-phenylacetamide (12),
2-(1,3-benzodioxol-5-yl)-2-(3-carbamimidoylphenoxy)-N-(2'-methanesulfonylbiphenyl-4-yl)acetamide (13),
2-(3-carbamimidoylphenoxy)-N-(2'-methanesulfonylbiphenyl-4-yl)-4-phenylbutyramide (14),
2-(3-carbamimidoylphenoxy)pentanoic acid (2'-methanesulfonylbiphenyl-4-ylmethyl)amide (15),
2-(3-carbamimidoylphenoxy)-4-methylpentanoic acid (2'-methanesulfonylbiphenyl-4-ylmethyl)amide (16);
2-(3-carbamimidoylphenoxy)-N-(2'-methanesulfonylbiphenyl-4-ylmethyl)-2-phenylacetamide (17),
3-(3-carbamimidoylphenyl)-N-(2'-methanesulfonylbiphenyl-4-yl)propionamide (18),
2-(3-carbamimidoylbenzyl)pentanoic acid (2'-methanesulfonylbiphenyl-4-yl)amide (19),
3-(3-carbamimidoylphenyl)-N-(2'-methanesulfonylbiphenyl-4-yl)-2-phenylpropionamide (20),
3-(3-carbamimidoylphenyl)-N-(2'-ethanesulfonylbiphenyl-4-yl)-2-phenylpropionamide (21),
3-(3-carbamimidoylphenyl)-N-(2'-ethanesulfonylbiphenyl-4-yl)-2-(3-methoxyphenyl)propionamide (22),
2-benzyl-3-(3-carbamimidoylphenyl)-N-(2'-methanesulfonylbiphenyl-4-yl)propionamide (23),
2-benzyl-3-(3-carbamimidoylphenyl)-N-(2'-ethanesulfonylbiphenyl-4-yl)propionamide (24),
2-(3-carbaminidoylbenzyl)-N-(2'-methanesulfonylbiphenyl-4-yl)butyramide (25),
2-(3-carbaminidoylbenzyl)hexanoic acid(2'-methanesulfonylbiphenyl-4-yl)amide (26),
2-(3-carbamimidoyl)-4-methylpentanoic acid(2'-methanesulfonylbiphenyl-4-yl)amide (27),
methyl (1-imino-1-(3-(1-(2'-methanesulfonylbiphenyl-4-ylcarbamoyl)butoxy)phenyl)methyl)carbamate (28),
2-(3-carbamimidoylphenoxy)pentanoicacid (2'-methoxybiphenyl-4-yl)amide (29),
2-[3-(N-hydroxycarbamimidoyl)phenoxy]pentanoic acid (2'-methanesulfonylbiphenyl-4-yl)amide (30),
2-(3-carbamimidoylphenoxy)pentanoic acid(2'-trifluoromethylbiphenyl-4-yl)amide (31).
ethyl(1-imino-1-{3-[1-(2'-methansulfonylbiphenyl-4-ylcarbamoyl)butoxy]phenyl}methyl)carbamate (32),
2-[3-(N-pentanoyloxycarbamimidoyl)phenoxy]pentanoic acid-(2'-methansulfonylbiphenyl-4-yl)amide (33),
2-[3-(N-(2-methylpropionyloxy)carbamimidoyl)phenoxyl]pentanoic acid (2'-methansulfonylbiphenyl-4-yl)amide (34),
2-[3-(N-benzoyloxycarbamimidoyl)phenoxyl]pentanoic acid(2'-methansulfonylbiphenyl-4-yl)amide (35),
2-[3-(N-acetoxycarbamimidoyl)phenoxy]pentanoic acid(2'-methansulfonylbiphenyl-4-yl)amide (36),
isobutyl(1-imino-1-{3-[1-(2'-methansulfonylbiphenyl-4-ylcarbamoyl)butoxy]phenyl}methyl)carbamate (37),
butyl(1-uimino-1-{3-[1-(2'-methansulfonylbiphenyl-4-ylcarbamoyl)butoxy]phenyl}methyl)carbamate (38),
isopropyl(1-imino-1-{3-[1-(2'-methansulfonylbiphenyl-4-ylcarbamoyl)butoxy]phenyl}methyl)carbamate (39),
2-[3-(N-methoxycarbaminidoyl)phenoxy]pentanoic acid(2'-methansulfonylbiphenyl-4-yl)amide (40),
(S)-2-[3-(N-hydroxycarbaminidoyl)phenoxy]pentanoic acid (2'-methansulfonylbiphenyl-4-yl)amide (41),
(R)-2-[3-(N-hydroxycarbamimidoyl)phenoxy]pentanoic acid(2'-methansulfonylbiphenyl-4-yl)amide (42),
methyl(1-imino-1-{3-[(S)-1-(2'-methansulfonylbiphenyl-4-ylcarbamoyl)butoxy]phenyl}methyl)carbamate (43),
2-(3-carbamimidoylphenoxy)pentanoic acid(2'-methansulfonylbiphenyl-2-ylmethyl)amide (44),
2-(3-carbamimidoylphenoxy)-N-(2'-methansulfonylbiphenyl-2-ylmethyl)-2-phenylacetamide (45),
2-(3-carbamimidoylphenoxy)-4-methylpentanoic acid-(2'-methansulfonylbiphenyl-2-ylmethyl)amide (46),
4-(3-carbamimidoylphenoxy)-N-(2'-methanesulfonylbiphenyl-4-yl)butyramide (47),
2-(7-carbamimidoyinaphthalin-2-yloxy)-N-(2'-methanesulfonylbiphenyl-4-yl)-2-phenylacetamide (48),
3-(3-carbamimidoylphenoxy)-N-(2'-methanesulfonylbiphenyl-4-yl)propionamide (49),
2-(3-carbamimidoylphenyl)pentanoic acid(2'-methansulfonylbiphenyl-4-yl)amide (50),
4-(3-carbamimidoylphenyl)-N-(2'-methansulfonylbiphenyl-4-yl)butyramide (51),
3-[3-(N-hydroxycarbamimidoyl)phenyl]-N-(2'-methansulfonylbiphenyl-4-yl)propionamide (52),
2-(3-carbamimidoylphenoxy)pentanoic acid(3-fluor-2'-methansulfonylbiphenyl-4-yl)amide (53).

The FAB values of these compounds are listed in the following tables. If not stated otherwise, the compounds were in each case prepared as acetates.

TABLE 1

Measured FAB values of synthesized active compounds

| No. | R⁵ | A | FAB |
|---|---|---|---|
| 1 | —H | —CH₃ | 424 |
| 2 | —CH₂CH₃ | —CH₃ | 466 |
| 3 | —CH₂CH₂CH₃ | —CH₃ | 466 |
| 4 | —CH₂CH₂CH₃ (wedge) | —CH₃ | 466 |
| 5 | —CH₂CH₂CH₃ (hashed) | —CH₃ | 466 |
| 6 | —CH₂CH₂CH₃ | —CH₂CH₂CH₃ | 480 |
| 7 | —CH₂CH₂CH₂CH₃ | —CH₃ | 480 |
| 8 | —CH₂CH₂CH₂CH₂CH₃ | —CH₃ | 494 |
| 9 | —CH(CH₃)₂ | —CH₃ | 466 |
| 10 | —CH₂CH(CH₃)₂ | —CH₃ | 480 |
| 11 | —phenyl | —CH₃ | 450 |
| 12 | —phenyl | —CH₂CH₂CH₃ | 514 |
| 13 | —benzo[1,3]dioxole | —CH₃ | 544 |
| 14 | —CH₂CH₂-phenyl | —CH₃ | 528 |

TABLE 2

Measured FAB values of synthesized active compounds

| Nr | R⁵ | A | FAB |
|---|---|---|---|
| 18 | —H | —CH₃ | 422 |
| 19 | —CH₂CH₂CH₃ | —CH₃ | 464 |
| 20 | —phenyl | —CH₃ | 489 |
| 21 | —phenyl | —CH₂CH₂CH₃ | 512 |
| 22 | —(3-methoxyphenyl) | —CH₂CH₂CH₃ | 542 |
| 23 | —CH₂-phenyl | —CH₃ | 512 |
| 24 | —CH₂-phenyl | —CH₂CH₂CH₃ | 526 |
| 25 | —CH₂CH₃ | —CH₃ | 450 |
| 26 | —CH₂CH₂CH₂CH₃ | —CH₃ | 478 |

TABLE 2-continued

Measured FAB values of synthesized active compounds

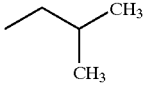

| Nr | R⁵ | A | FAB |
|----|-----|------|-----|
| 27 | isobutyl (CH(CH₃)CH₂CH₃-like, sec-butyl) | —CH₃ | 478 |

TABLE 3

Measured FAB values of synthesized active compounds

| No. | R⁵ | A | FAB |
|-----|-----|------|-----|
| 15 | n-butyl (—CH₂CH₂CH₂CH₃) | —CH₃ | 480 |
| 16 | isobutyl (—CH₂CH(CH₃)₂) | —CH₃ | 494 |
| 17 | phenyl | —CH₃ | 514 |

TABLE 4

Measured FAB values of synthesized active compounds (structure: R¹-phenyl-O-CH(R⁵)-C(O)-NH-phenyl-biphenyl-R²)

| Nr | R¹ | R⁵ | R² | FAB |
|----|-----|-----|-----|-----|
| 28 | —C(=NH)NH-C(O)-O-CH₃ | n-butyl | —S(O)₂—CH₃ | 524 |
| 29 | —C(=NH)NH₂ | n-butyl | —O—CH₃ | 418 |
| 30 | —C(=N-OH)NH₂ | n-butyl | —S(O)₂—CH₃ | 482 |
| 31 | —C(=NH)NH₂ | n-butyl | —CF₃ | 456 |
| 32 | —C(=NH)NH-C(O)-O-CH₂CH₃ | n-butyl | —S(O)₂—CH₃ | 538 |

TABLE 4-continued
Measured FAB values of synthesized active compounds
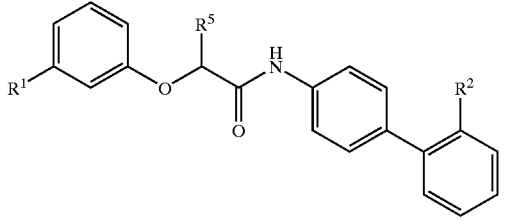
| Nr | R¹ | R⁵ | R² | FAB |
|---|---|---|---|---|
| 33 | 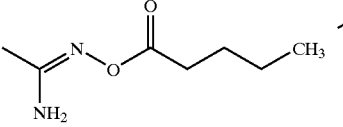 | 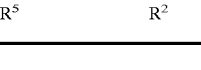 | 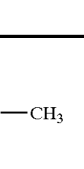 | 566 |
| 34 | 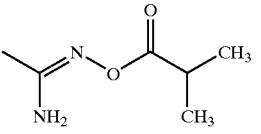 | 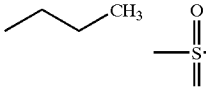 |  | 552 |
| 35 | 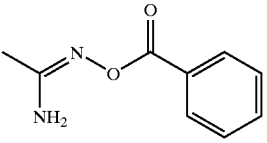 | 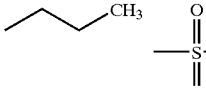 |  | 586 |
| 36 | 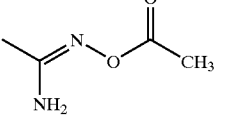 | 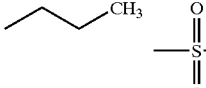 |  | 524 |
| 37 | 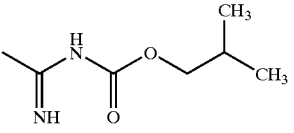 | 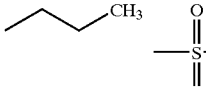 |  | 566 |
| 38 | 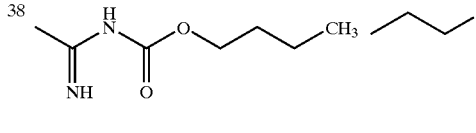 | 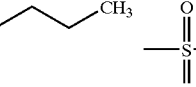 |  | 566 |
| 39 | 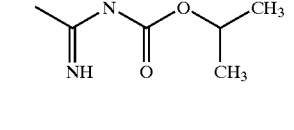 | 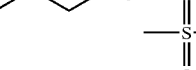 |  | 552 |

TABLE 4-continued
Measured FAB values of synthesized active compounds
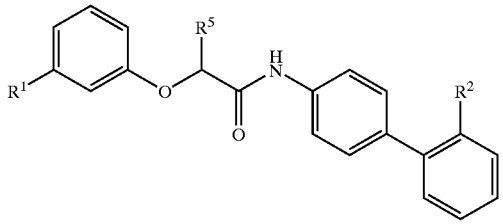
| Nr | R¹ | R⁵ | R² | FAB |
|---|---|---|---|---|
| 40 | 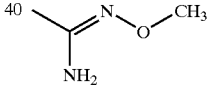 | 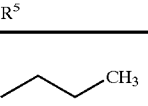 | 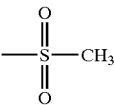 | 496 |
| 41 | 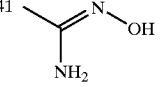 | 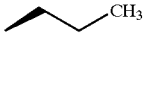 | 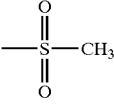 | 482 |
| 42 | 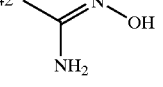 | 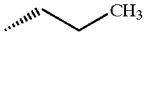 | 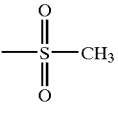 | 482 |
| 43 | 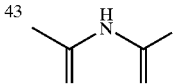 | 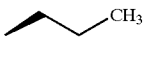 | 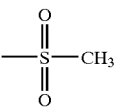 | 524 |
TABLE 5
Measured FAB valves of synthesized acitve compounds
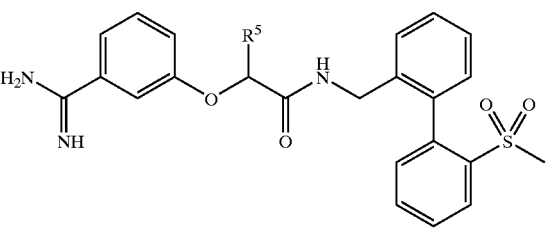
| Nr. | R⁵ | FAB |
|---|---|---|
| 44 | 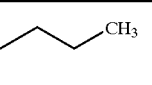 | 480 |
| 45 | 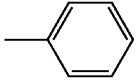 | 514 |
TABLE 5-continued
Measured FAB valves of synthesized acitve compounds
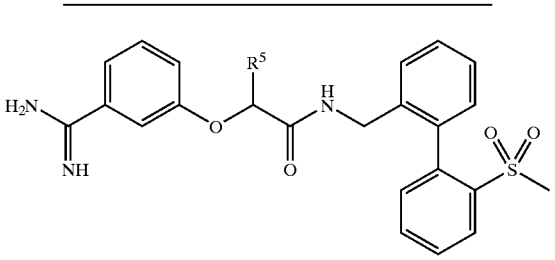
| Nr. | R⁵ | FAB |
|---|---|---|
| 46 | 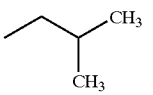 | 494 |

TABLE 6

Measured FAB valves of synthesized active compounds

| Nr. | Struktur | FAB |
|---|---|---|
| 47 | | 452 |
| 48 | | 550 |
| 49 | | 538 |
| 50 | | 450 |
| 51 | | 436 |
| 52 | | 438 |

TABLE 6-continued

Measured FAB valves of synthesized active compounds

| Nr. | Struktur | FAB |
|---|---|---|
| 53 | | 484 |

The invention further relates to the use of the compounds of the formula I and/or their physiologically acceptable salts for the production of pharmaceutical preparations, in particular in a non-chemical way. In this connection, they can be brought into a suitable dose form together with at least one solid, liquid and/or semi-liquid vehicle or excipient and, if appropriate, in combination with one or more further active compounds.

The invention further relates to pharmaceutical preparations comprising at least one compound of the formula I and/or one of its physiologically acceptable salts.

These preparations can be used as medicaments in human or veterinary medicine. Suitable vehicles are organic or inorganic substances which are suitable for enteral (e.g. oral) or parenteral administration or topical application and do not react with the novel compounds, for example water, vegetable oils, benzyl alcohols, alkylene glycols, polyethylene glycols, glyceryl triacetate, gelatine, carbohydrates such as lactose or starch, magnesium stearate, talc and petroleum jelly. In particular, tablets, pills, coated tablets, capsules, powders, granules, syrups, juices or drops are used for oral administration, suppositories are used for rectal administration, solutions, preferably oily or aqueous solutions, furthermore suspensions, emulsions or implants, are used for parenteral administration, and ointments, creams or powders are used for topical application. The novel compounds can also be lyophilized and the lyophilizates obtained used, for example, for the production of injection preparations. The preparations indicated can be sterilized and/or can contain excipients such as lubricants, preservatives, stabilizers and/or wetting agents, emulsifiers, salts for influencing the osmotic pressure, buffer substances, colorants, flavourings and/or one or more further active compounds, e.g. one or more vitamins.

The compounds of the formula I and their physiologically acceptable salts can be used in the control and prevention of thromboembolic conditions such as thrombosis, myocardial infarct, arteriosclerosis, inflammation, apoplexy, angina pectoris, restenosis after angioplasty and intermittent claudication.

In this case, the substances according to the invention are as a rule preferably administered in doses of between approximately 1 and 500 mg, in particular between 5 and 100 mg, per dose unit. The daily dose is preferably between approximately 0.02 and 10 mg/kg of bodyweight. The specific dose for each patient depends, however, on all sorts of factors, for example on the efficacy of the specific compound employed, on the age, bodyweight, general state of health, sex, on the diet, on the time and route of administration, on the excretion rate, pharmaceutical combination and severity of the particular condition to which the therapy applies. Oral administration is preferred.

The compounds of the formula I and also the starting substances for their preparation are prepared by methods known per se, such as are described in the literature (e.g. in the standard works such as Houben-Weyl, Methoden der organischen Chemie, Georg-Thieme-Verlag, Stuttgart (Methods of Organic Chemistry)), namely under reaction conditions which are known and suitable for the reactions mentioned. Use can also be made in this case of variants which are known per se but not mentioned here in greater detail.

If desired, the starting substances can also be formed in situ, such that they are not isolated from the reaction mixture, but immediately reacted further to give the compounds of the formula I. In the following, a synthesis is generally presented with which compounds of the formula I can be prepared. For the preparation of specific compounds, the synthesis can be varied by the choice of suitable starting compounds. The synthesis is only intended to show, by way of example, one possible route for the preparation of the compounds of the formula I. It is also possible, however, to use other synthetic routes for preparation.

FIG.1: Synthesis of Inventive Compounds

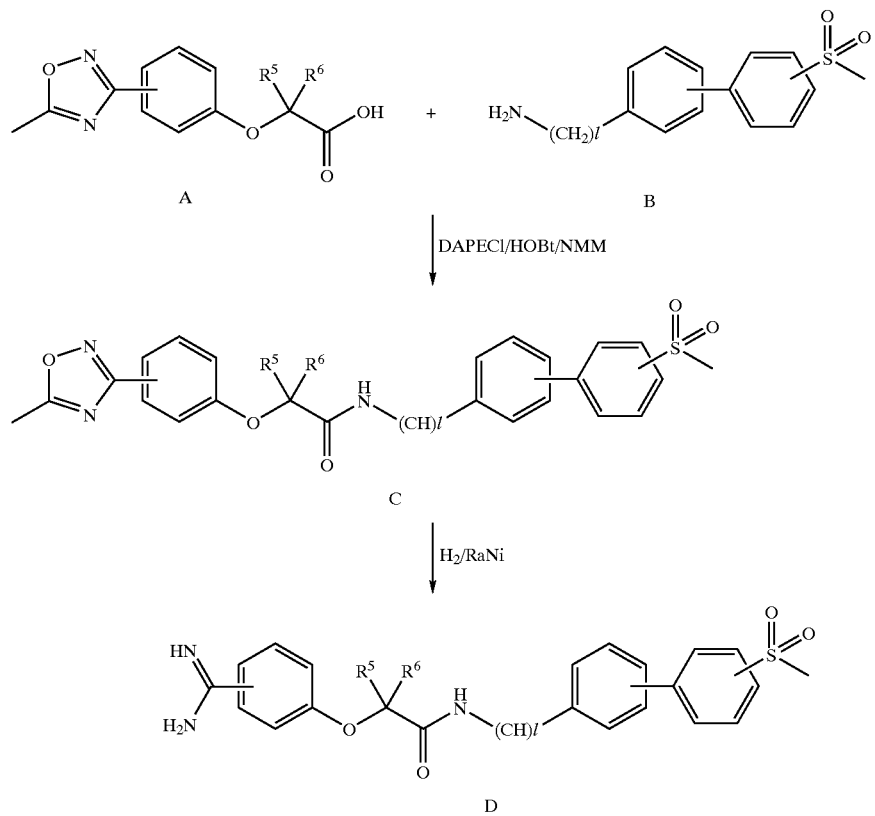

An examplary synthesis is shown in FIG. 1.

The protected acid unit A is reacted with the amine B, with formation of a central amide bond, to form the compound C. The carbamimidoyl group is then liberated reductively to give the inventive compound D.

The acid unit A and the amine B are likewise preparable by common syntheses. An exemplary synthesis is presented below in FIG. 2.

FIG. 2: Synthesis of an Acid Unit;
[3-(5-Methyl[1,2,4]oxadiazol-3-yl)phenoxy]-2-phenylacetic acid

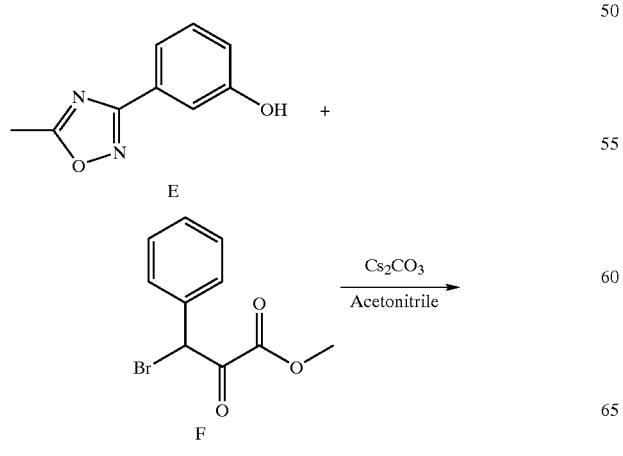

For the synthesis of the acid unit, the phenol derivative E protected on the carbamimidoyl group is reacted with the protected α-bromocarboxylic acid F to give the compound G. The ester G is then hydrolysed to the carboxylic acid A'.

The amines B can be prepared, for example, in the following way (FIG. 3).

FIG. 3: Synthesis of 2-methanesulfonylbiphenyl-4-ylamine

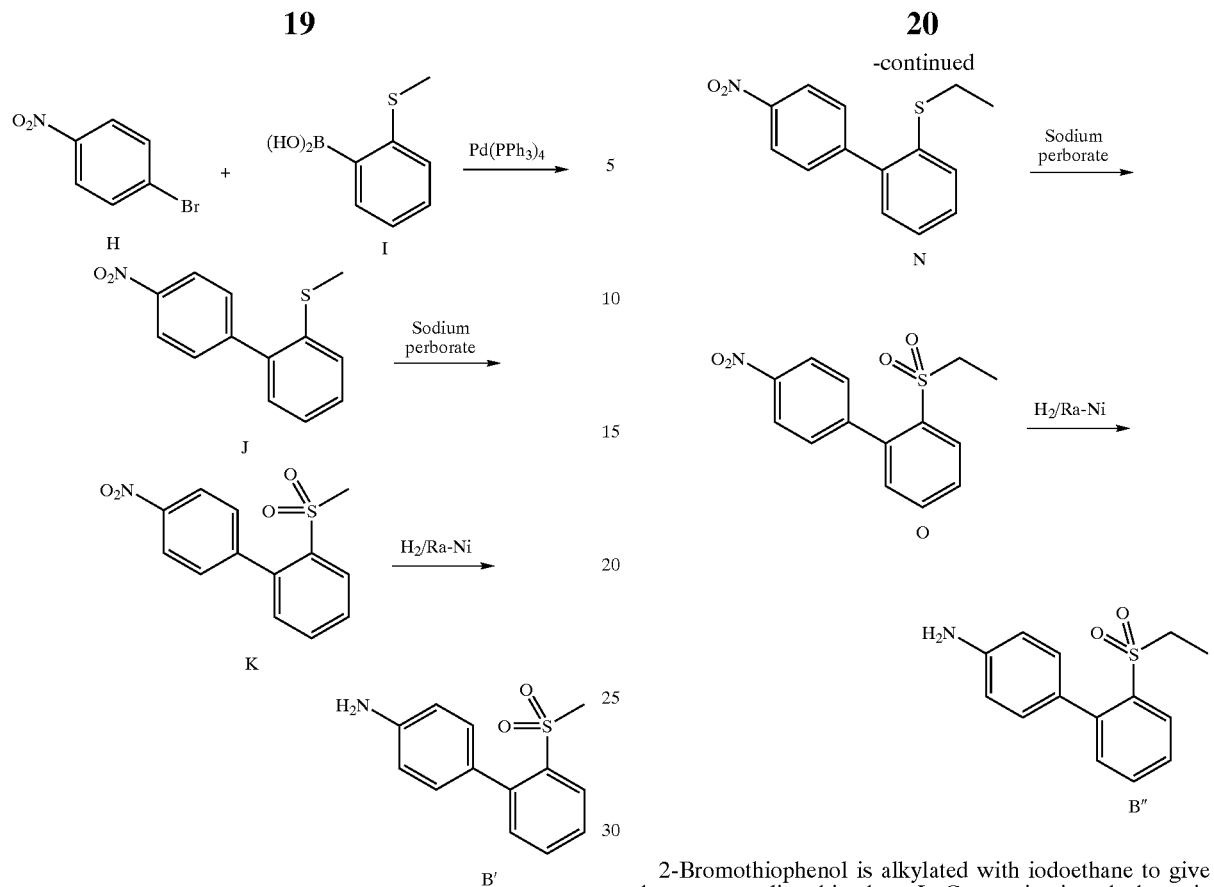

Bromonitrobenzene H is reacted with the boronic acid derivative I to give the biphenyl derivative J. The methylthio group of the biphenyl derivative I is then reacted with a suitable oxidizing agent such as sodium perborate to give the methanesulfonyl compound K. In a further step, the nitro group is reduced to the amine with attainment of the amine unit B'. According to an analogous synthesis route, it is also possible to prepare the corresponding ethanesulfonyl compounds (FIG. 4).

FIG. 4: Synthesis of 2'-ethanesulfonylbiphenyl-4-ylamine

2-Bromothiophenol is alkylated with iodoethane to give the corresponding thioethane L. Conversion into the boronic acid M then takes place and is followed, as already in the synthesis from FIG. 3, by the linkage of a carbon bond to the biphenyl derivative N. The oxidation to the ethanesulfonyl compound is carried out and is followed by the reduction of the nitro group to the amine derivative B''. The preparation of a biphenylamine which comprises a $CF_3$ group can be carried out by appropriate choice of the starting materials analogously to the syntheses shown in FIGS. 3 and 4. The synthesis is shown in FIG. 5.

FIG.5 Synthesis of 2-trifluoromethylbiphenyl-4-ylamine

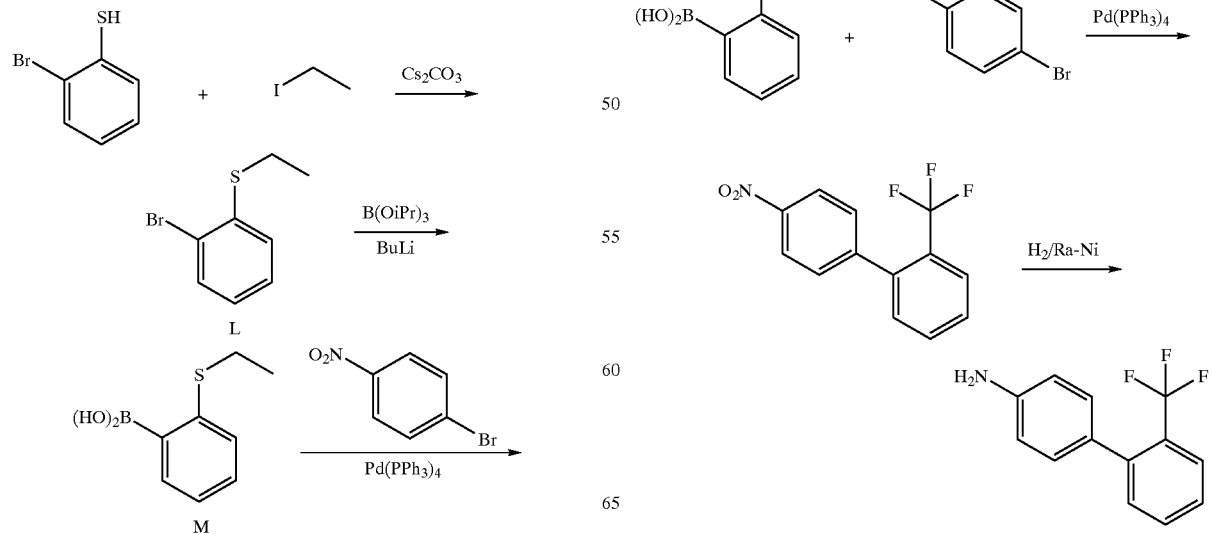

The synthesis of the methoxy derivative, which is shown in FIG. 6, also proceeds analogously.

FIG. 6 Synthesis of 2'-methoxybiphenyl-4-ylamine

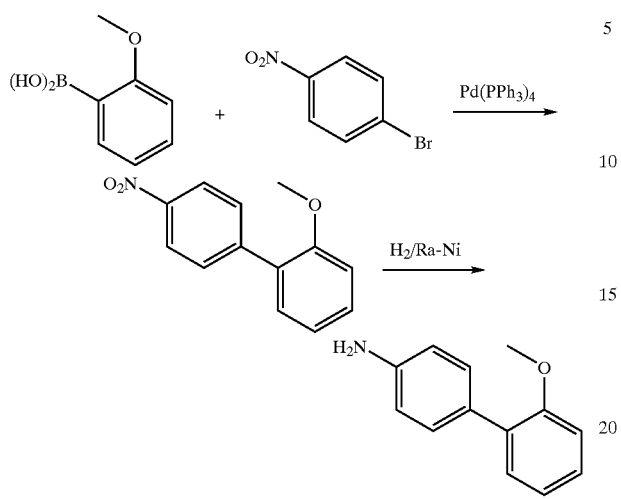

The methylamine derivatives of the biphenyl moiety can be prepared from the corresponding nitrile compounds. An exemplary synthesis is shown in FIG. 7.

FIG. 7 Synthesis of biphenyl-4-ylmethylamine derivatives

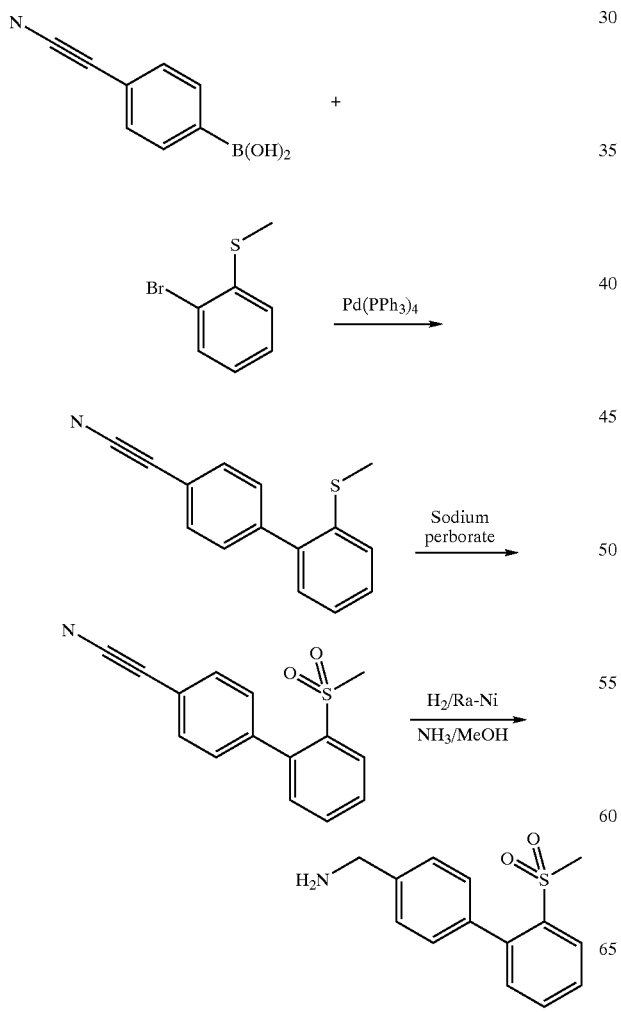

The synthesis of active compounds having a modified carbamimidoyl group is shown by way of example in FIGS. 8 and 9.

FIG. 8 Synthesis of 2-[3-(N-hydroxycarbamimidoyl)phenoxy]pentanoic acid (2'-methanesulfonylbiphenyl-4-yl)amide (27)

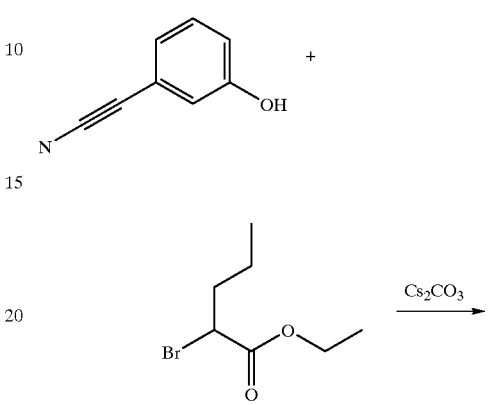

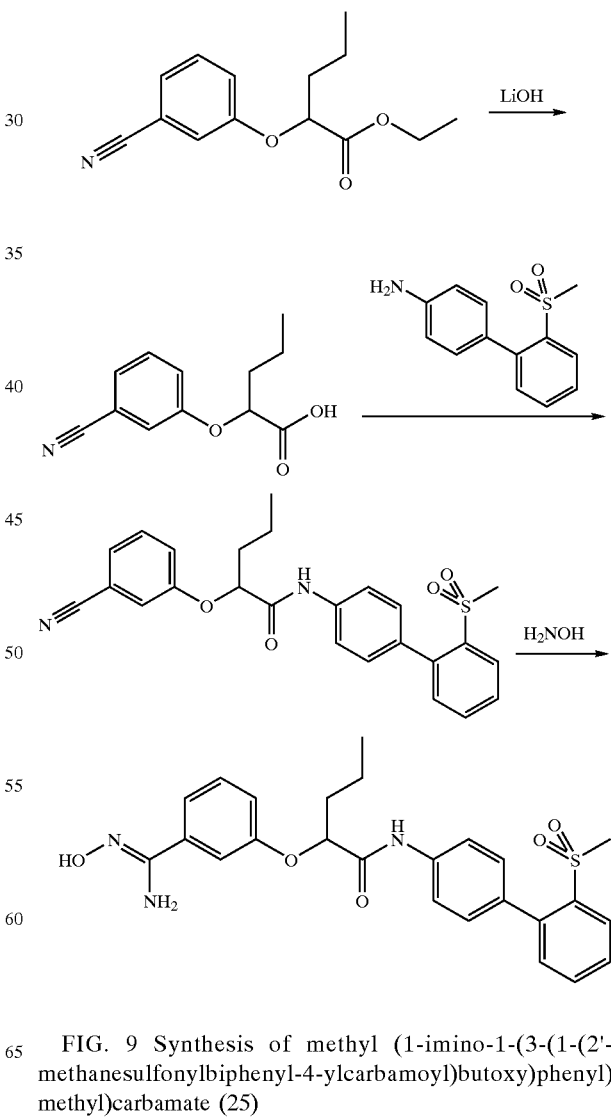

FIG. 9 Synthesis of methyl (1-imino-1-(3-(1-(2'-methanesulfonylbiphenyl-4-ylcarbamoyl)butoxy)phenyl)methyl)carbamate (25)

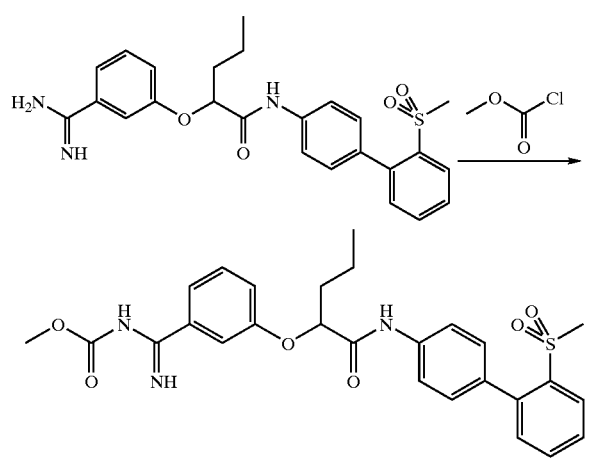

The synthesis routes shown can be easily varied by the person skilled in the art, for example by suitably modifying the substitution pattern of the individual synthesis units.

The invention is illustrated in greater detail with the aid of examples.

EXAMPLE 1

[3-(5-Methyl[1,2,4]oxadiazol-3-yl)phenoxy]-2-phenylacetic acid a) Methyl[3-(5-methyl[1,2,4]oxadiazol-3-yl)phenoxy]-2-phenylacetate A solution of 1.00 g (5.68 mmol) of 3-(5-methyl-[1,2,4]oxadiazol-3-yl)phenoxy]-2-phenol and 0.90 ml (5.7 mmol) of methyl 2-bromo-2-phenylacetate in 20 ml of acetonitrile is treated with 1.96 g (6.00 mmol) of caesium carbonate and stirred at room temperature for 18 hours. The reaction mixture is filtered and the filtrate is evaporated. A colourless solid is obtained; FAB 325.

b) [3-(5-Methyl[1,2,4)]oxadiazol-3-yl)phenoxy]-2-phenylacetic acid

A solution of 1.77 g (5.46 mmol) of methyl [3-(5-methyl [1,2,4]oxadiazol-3-yl)phenoxy]-2-phenylacetate in 15 ml of methanol is treated with 10 ml of 1 N aqueous sodium hydroxide solution and heated at 80° C. for 3 hours. The reaction mixture is concentrated and the residue is treated with 1 N hydrochloric acid. It is extracted with ethyl acetate and the organic phase is evaporated. A colourless solid is obtained; FAB 311

EXAMPLE 2

2'-Methanesulfonylbiphenyl-4-ylamine a) 2-Methylsulfanyl-4'-nitrobiphenyl

A solution of 30.3 g (150 mmol) of 1-bromo-4-nitrobenzene and 25.0 g (149 mmol) of 2-methylthiobenzeneboronic acid in a mixture of 300 ml of methanol and 500 ml of toluene is treated with 16.0 g (150 mmol) of sodium carbonate and 5.0 g (4.3 mmol) of tetrakis(triphenylphosphine)palladium and heated at 100° C. for 18 hours. The reaction mixture is partitioned between water and ethyl acetate, the organic phase is dried and evaporated and the residue is recrystallized from petroleum ether/ethyl acetate. A yellowish solid is obtained; FAB 246 b) 2-Methanesulfonyl-4'-nitrobiphenyl

A solution of 20.0 g (81.5 mmol) of 2-methylsulfanyl-4'-nitrobiphenyl in 150 ml of glacial acetic acid is treated with 66 g of sodium perborate trihydrate and heated at 60° C. with stirring for 3 days. The reaction mixture is added to water, and the precipitate is filtered off and recrystallized from petroleum ether/ethyl acetate. A yellowish solid is obtained; FAB 278 c) 2'-Methanesulfonylbiphenyl-4-ylamine

A solution of 17.0 g (61.3 mmol) of 2-methanesulfonyl-4'-nitrobiphenyl in 170 ml of THF is treated with 3.5 g of THF-moist Raney nickel and hydrogenated at room temperature and normal pressure until the completion of hydrogen absorption (18 hours). The catalyst is filtered off and the filtrate is evaporated. A colourless solid is obtained; FAB 248

EXAMPLE 3

2'-Ethanesulfonylbiphenyl-4-ylamine a) 1-Bromo-2-ethylsulfanyl-1-benzene

A solution of 10 ml (85 mmol) of 2-bromothiophenol and 6.9 ml (85 mmol) of iodoethane in 50 ml of acetonitrile is treated with 28 g (85 mmol) of caesium carbonate and stirred at room temperature for 18 hours. The reaction mixture is filtered and the filtrate is evaporated. FAB218 b) 2-Ethylsulfanylbenzeneboronic acid 9.5 g (50 mmol) of triisopropyl borate are added to a solution of 10.9 g (50.0 mmol) of 1-bromo-2-ethylsulfanylbenzene kept at −70° C. 33.3 ml of a 15% solution of BuLi in hexane (55 mmol) are then added. The mixture is stirred at −70° C. for a further 30 minutes, then 1 N hydrochloric acid and ethyl acetate are added. The organic phase is separated off, dried and evaporated. The residue is taken up in diethyl ether and filtered. A colourless solid is obtained; FAB 182

Further synthesis follows Example 2.

EXAMPLE 4

C-(2'-Methanesulfonylbiphenyl-4-yl)methylamine a) 2'-Methanesulfonylbiphenyl-4-carbonitrile A solution of 1.0 g (4.9 mmol) of 2-bromothioanisole and 1.5 g (10 mmol) of 4-cyanobenzeneboronic acid in a mixture of 50 ml of toluene and 30 ml of methanol is treated with 1.1 g (10 mmol) of sodium carbonate and 0.5 g (0.43 mmol) of tetrakis(triphenylphosphine)palladium and heated at 100° C. for 18 hours. The reaction mixture is partitioned between water and ethyl acetate. The organic phase is evaporated and chromatographed on a silica gel column using petroleum ether/ethyl acetate. A colourless solid is obtained; FAB 226 b) 2'-Methanesulfonylbiphenyl-4-carbonitrile

A solution of 1.0 g (4.4 mmol) of 2'-methanesulfonylbiphenyl-4-carbonitrile in 10 ml of glacial acetic acid is treated with 3.2 g of sodium perborate trihydrate and stirred at room temperature for 48 hours. The reaction mixture is added to water and the precipitate is filtered off. A colourless solid is obtained; FAB 258 c) C-(2'-Methanesulfonylbiphenyl-4-yl)methylamine

A solution of 1.0 g (3.9 mmol) of 2'-methanesulfonylbiphenyl-4-carbonitrile in a mixture of 10 ml of methanol saturated with ammonia and 3 ml of THF is treated with 400 mg of Raney nickel and hydrogenated at room temperature and normal pressure. The catalyst is filtered off and the filtrate is evaporated. A colourless solid is obtained; FAB 262

EXAMPLE 5

2-(3-Carbamimidoylphenoxy)-N-(2'-methanesulfonylbiphenyl-4-yl)-2-phenylacetamide a) N-(2'-Methanesulfonylbiphenyl-4-yl)-2-[3-(5-methyl[1,2,4]oxadiazol-3-yl)phenoxy]2-phenylacetamide A solution of 102 mg (0.330 mmol) of [3-(5-methyl[1,2,4]]oxadiazol-3-yl)phenoxy]-2-phenylacetic acid, 81.6 mg (0.330 mmol) of 2'-methanesulfonylbiphenyl-4-ylamine, 63.3 mg (0.330 mol) of N-(3-dimethylaminopropyl)-N'-ethylcarbodiimide hydrochloride (DAPECI) and 44.6 mg (0.330 mmol) of 1-hydroxybenzotriazole (HOBt) in 5 ml of DMF is treated with 0.036 ml (0.33 mmol) of 4-methylmorpholine and stirred at room temperature for 18 hours. The reaction mixture is added to water and the precipitate is filtered off. A colourless solid is obtained; FAB 540 b) 2-(3-Carbamimidoylphenoxy)-N-(2'-methanesulfonylbiphenyl-4-yl)-2-phenylacetamide acetate (11)

A solution of 150 mg (0.278 mmol) of N-(2'-methanesulfonylbiphenyl-4-yl)-2-[3-(5-methyl-[1,2,4]oxadiazol-3-yl)phenoxy]-2-phenylacetamide in 7 ml of methanol is treated with 100 mg of water-moist Raney nickel and 70 mg of acetic acid and hydrogenated for 18 hours at room temperature and normal pressure. The reaction mixture is filtered, the filtrate is evaporated and the residue is stirred with diethyl ether. A colourless solid is obtained; FAB 500

EXAMPLE 6

2-[3-(N-Hydroxycarbamimidoyl)phenoxy]pentanoic acid (2'-methanesulfonylbiphenyl-4-yl)amide hydrochloride (27)

a) Ethyl 2-(3-cyanophenoxy)pentanoate

A solution of 5.0 g (42 mmol) of 3-hydroxybenzonitrile and 8.78 g (42.0 mmol) of ethyl 2-bromovalerate in 80 ml of acetonitrile is treated with 13.7 g (42.0 mmol) of caesium carbonate and stirred at room temperature for 18 hours. The reaction mixture is filtered off and the filtrate evaporated. A colourless oil is obtained; FAB 248 b) 2-(3-Cyanophenoxy)pentanoic acid

A solution of 9.00 g (36.5 mmol) of ethyl 2-(3-cyanophenoxy)pentanoate in 10 ml of methanol is treated with a solution of 1.29 g (54.0 mmol) of lithium hydroxide in 10 ml of water and the mixture is stirred at room temperature for 18 hours. The reaction mixture is concentrated in vacuo, extracted with ethyl acetate, and the aqueous phase is acidified and extracted with ethyl acetate. The organic phase is dried over sodium sulfate and evaporated. A colourless solid is obtained; FAB 220 c) 2-(3-Cyanophenoxy)pentanoic acid) (2'-methanesulfonylbiphenyl-4-yl)amide

A solution of 2.26 g (9.12 mmol) of 2'-methanesulfonylbiphenyl-4-ylamine, 2.00 g (9.12 mmol) of 2-(3-cyanophenoxy)pentanoic acid, 1.75 g (9.12 mmol) of N-(3-dimethylaminopropyl)-N'-ethylcarbodiimide hydrochloride, 1.23 g (9.12 mmol of 1-hydroxybenzotriazole and 1.00 ml (9.12 mmol) of 4-methylmorpholine in 5 ml of DMF is stirred at room temperature for 18 hours. The reaction mixture is treated with water and the resulting precipitate is filtered off. A colourless solid is obtained; FAB 449 d) 2-[3-(N-Hydroxycarbamimidoyl)phenoxy]pentanoic acid (2'-methanesulfonylbiphenyl-4-yl)amide A solution of 1.40 g (3.12 mmol) of 2-(3-cyanophenoxy) pentanoic acid (2'-methanesulfonylbiphenyl-4-yl)amide in 50 ml of methanol is treated with 695 mg (10.0 mmol) of hydroxylammonium chloride hydrochloride and 1.01 g (10.0 mmol) of triethylamine and stirred at 60° C. for 18 hours. It is allowed to cool, the solvent is stripped off, the residue is taken up in water and the resulting precipitate is filtered off. A colourless solid is obtained; FAB 482 e) 2-[3-(N-Hydroxycarbamimidoyl)phenoxy]pentanoic acid (2'-methanesulfonylbiphenyl-4-yl)amide hydrochloride (27)

A solution of 100 mg (0.208 mmol) of 2-[3-(N-hydroxycarbamimidoyl)phenoxy]pentanoic acid (2'-methanesulfonylbiphenyl-4-yl)amide in 5 ml of methanol is treated with 2.08 ml of a 0.1 N solution of hydrogen chloride in isopropanol. The solution is evaporated. A colourless solid is obtained; FAB 482

EXAMPLE 7 methyl(1-imino-1-{3-[1-(2'-methanesulfonylbiphenyl-4-ylcarbamoyl)butoxy]phenyl}methyl)carbamate 1 N NaOH is added up to a pH of 9 to a solution of 500 mg (1.07 mmol) of 2-(3-carbamimidoylphenoxy) pentanoic acid (2'-methanesulfonylbiphenyl-4-yl)amide acetate (3) in 40 ml of dichloromethane kept at 5° C. 0.108 ml (1.40 mmol) of methyl chloroformate is then added. During the following hour, the pH is kept at a value of 9 by addition of further 1 N NaOH. The organic phase is then separated off, washed with water, dried over sodium sulfate and evaporated. A colourless solid is obtained; FAB 524

The following examples relate to pharmaceutical preparations.

EXAMPLE A

Injection Vials

A solution of 100 g of an active compound of the formula I and 5 g of disodium hydrogen phosphate is adjusted to pH 6.5 in 3 l of double-distilled water using 2 N hydrochloric acid, sterile filtered, dispensed into injection vials, lyophilized under sterile conditions and aseptically sealed. Each injection vial contains 5 mg of active compound.

EXAMPLE B

Suppositories

A mixture of 20 g of an active compound of the formula I is fused with 100 g of soya lecithin and 1400 g of cocoa butter, poured into moulds and allowed to cool. Each suppository contains 20 mg of active compound.

EXAMPLE C

Solution

A solution is prepared from 1 g of an active compound of the formula I, 9.38 g of $NaH_2PO_4$ 2 $H_2O$, 28.48 g of $Na_2HPO_4$ 12 $H_2O$ and 0.1 g of benzalkonium chloride in 940 ml of double-distilled water. It is adjusted to pH 6.8, made up to 1 l and sterilized by irradiation. This solution can be used in the form of eye drops.

EXAMPLE D

Ointment 500 mg of an active compound of the formula I are mixed with 99.5 g of petroleum jelly under aseptic conditions.

EXAMPLE E

Tablets

A mixture of 1 kg of active compound of the formula I, 4 kg of lactose, 1.2 kg of potato starch, 0.2 kg of talc and 0.1 kg of magnesium stearate is compressed in a customary manner to give tablets such that each tablet contains 10 mg of active compound.

EXAMPLE F

Coated tablets

Analogously to Example E, tablets are pressed and are then coated in a customary manner with a coating of sucrose, potato starch, talc, tragacanth and colorant.

EXAMPLE G

Capsules 2 kg of active compound of the formula I are filled into hard gelatine capsules in a customary manner such that each capsule contains 20 mg of the active compound.

EXAMPLE H

Ampoules

A solution of 1 kg of active compound of the formula I in 60 l of double-distilled water is sterile filtered, dispensed into ampoules, lyophilized under sterile conditions and aseptically sealed. Each ampoule contains 10 mg of active compound.

What is claimed is:

1. A compound of the formula I

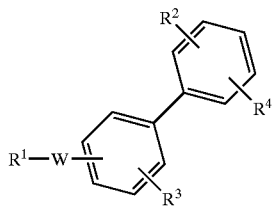

I in which:

$R^1$ is: phenyl or naphthyl, which is substituted by —C(=NH)NH$_2$, that is optionally monosubstituted by —COA, —CO[C(R$^7$)$_2$]$_n$-Ar', —COOA, —OR$^7$, —OCOA, —OCO—[C(R$^7$)$_2$]$_n$-Ar', —OH, an amino protective group, —NHC(=NH)—NH$_2$, —CON=C(NH$_2$)$_2$,

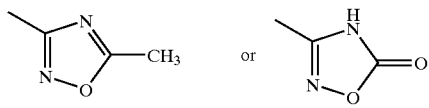

and which is optionally substituted by -A, —OR$^5$, —N(R$^5$)$_2$, —NO$_2$, —CN, —Hal, —NR$^5$COA, —NR$^5$COAr', —NR$^5$SO$_2$A, —NR$^5$SO$_2$Ar', —COOR$^5$, —CON(R$^5$)$_2$, —COR$^7$, —COAr' or S(O)$_n$A;

$R^2$ is: —S(O)$_n$A, —CF$_3$, —COOR$^7$, or —OA;

$R^3$, $R^4$ are: independently of one another —H, -A, —OR$^5$, —N(R$^5$)$_2$, —NO$_2$, —CN, —Hal, —NR$^5$COA, —NR$^5$COAr', —NR$^5$SO$_2$A, —NR$^5$SO$_2$Ar', —COOR$^5$, —CON(R$^5$)$_2$, —CONR$^5$Ar', —COR$^7$, —COAr', or —S(O)$_n$A;

$R^5$, $R^6$ are: independently of one another —H, -A, —[C(R$^7$R$^8$)]$_n$Ar' or —[C(R$^7$R$^8$)]$_n$Het;

$R^7$, $R^8$ are: independently of one another —H or -A;

W is: —[C(R$^5$R$^6$)]$_m$CONR$^5$[C(R$^5$R$^6$)]$_l$—, or —OC(R$^5$R$^6$)CONR$^5$[C(R$^5$R$^6$)]$_l$;

A is: alkyl having 1 to 20 C atoms, in which one or two CH$_2$ groups are optionally and independently replaced by O or S atoms or by —CH=CH— groups and wherein 1 to 7 H atoms are optionally replaced by —F;

Ar is: phenyl or naphthyl, which is unsubstituted or mono-, di- or trisubstituted by -A, -Ar'-, -Het, —OR$^5$, —N(R$^5$)$_2$, —NO$_2$, —CN, -Hal, —NR$^5$COA, —NR$^5$COAr, —NR$^5$SO$_2$A, —NR$^5$SO$_2$Ar', —COOR$^5$, —CON(R$^5$)$_2$, —CONR$^5$Ar', —COR$^7$, —COAr', —SO$_2$NR$^5$, —S(O)$_n$Ar' or —S(O)$_n$A;

Ar' is: phenyl or naphthyl, which is unsubstituted or mono-, di- or trisubstituted by -A, —OR$^7$, —N(R$^7$)$_2$, —NO$_2$, —CN, -Hal, —NR$^7$COA, —NR$^7$SO$_2$A, —COOR$^7$, —CON(R$^7$)$_2$, —COR$^7$, —SO$_2$NR$^7$ or —S(O)$_n$A;

Het is: a mono- or binuclear saturated, unsaturated or aromatic heterocycle having 1 to 4 N, O and/or S atoms, bonded via N or C, which is unsubstituted or mono-, di- or trisubstituted by -A, —OR$^7$, —N(R$^7$)$_2$, —NO$_2$, CN, -Hal, —NR$^7$COA, —NR$^7$SO$_2$A, —COOR$^7$, —CON(R$^7$)$_2$, —COR$^7$, SO$_2$NR$^7$, —S(O)$_n$A and/or carbonyl oxygen;

Hal is: —F, —Cl, —Br or —I;

l is: 0 or 1;

m is: 1, 2 or 3; and n is: 0, 1 or 2;

or a pharmaceutically acceptable salt or solvate thereof.

2. A compound according to claim 1 selected from the following compounds 2-(3-carbamimidoylphenoxy)-N-(2'-methanesulfonylbiphenyl-4-yl)acetamide (1), 2-(3-carbamimidoylphenoxy)-N-(2'-methanesulfonylbiphenyl-4-yl)butyramide (2), 2-(3-carbamimidoylphenoxy)pentanoic acid (2'-methanesulfonylbiphenyl-4-yl)amide (3), (S)-2-(3-carbamimidoylphenoxy)pentanoic acid (2'-methanesulfonylbiphenyl-4-yl)amide (4), (R)-2-(3-carbamimidoylphenoxy)pentanoic acid (2'-methanesulfonylbiphenyl-4-yl)amide (5), (2-(3-carbamimidoylphenoxy)pentanoic acid (2'-ethanesulfonylbiphenyl-4-yl)amide (6), (2-(3-carbamimidoylphenoxy)hexanoic acid (2'-methanesulfonylbiphenyl-4-yl)amide (7), (2-(3-carbamimidoylphenoxy)hexptanoic acid (2'-methanesulfonylbiphenyl4-yl)amide (8), 2-(3-carbamimidoylphenoxy)-N-(2'-methanesulfonylbiphenyl-4-yl)-3-methylbutyramide (9), 2-(3-carbamimidoylphenoxy)-4-methylpentanoic acid (2'-methanesulfonylbiphenyl-4-yl)amide (10), 2-(3-carbamimidoylphenoxy)-4-methylpentanoic acid (2'-methanesulfonylbiphenyl-4-yl)amide (11), 2-(3-carbamimidoylphenoxy)-N-(2'-ethanesulfonylbiphenyl-4-yl)-2-phenylacetamide (12), 2-(1,3-benzodioxol-5-yl)-2-(3-carbamimidoylphenoxy)-N-(2'-methanesulfonylbiphenyl-4-yl)acetamide (13), 2-(3-carbamimidoylphenoxy)-N-(2'-methanesulfonylbiphenyl-4-yl)-4-phenylbutyramide (14), 2-(3-carbamimidoylphenoxy)pentanoic acid (2'-methanesulfonylbiphenyl-4-ylmethyl)amide (15),
2-(3-carbamimidoylphenoxy)-4-methylpentanoic acid (2'-methanesulfonylbiphenyl-4-ytmethyl)amide (16);
2-(3-carbamimidoylphenoxy)-N-(2'-methanesulfonylbiphenyl-4-ylmethyl)-2-phenylacetamide (17),
3-(3-carbamimidoylphenyl)-N-(2'-methanesulfonylbiphenyl-4-yl)propionamide(18),
2-(3-carbamimidoylbenzyl)pentanoic acid (2'-methanesulfonylbiphenyl-4-yl)amide (19),
3-(3-carbamimidoylphenyl)-N-(2'-methanesulfonylbiphenyl-4-yl)-2-phenylpropionamide (20),
3-(3-carbamimidoylphenyl)-N-(2'-ethanesulfonylbiphenyl-4-yl)-2-phenylpropionamide (21),
3-(3-carbamimidoylphenyl)-N-(2'-ethanesulfonylbiphenyl-4-yl)-2-(3-methoxyphenyl)propionamide (22),
2-benzyl-3-(3-carbamimidoylphenyl)-N-(2'-methanesulfonylbiphenyl-4-yl)propionamide (23),
2-benzyl-3-(3-carbamimidoylphenyl)-N-(2'-ethanesulfonylbiphenyl-4-yl)propionamide (24),
2-(3-carbaminidoylbenzyl)-N-(2'-methanesulfonylbiphenyl-4-yl)butyramide (25),
2-(3-carbaminidoylbenzyl)hexanoic acid(2'-methanesulfonylbiphenyl-4-yl)amide (26),
2-(3-carbamimidoyl)-4-methylpentanoic acid(2'-methanesulfonylbiphenyl-4-yl)amide (27),
methyl(1-imino-1-(3-(1-(2'methanesulfonylbiphenyl-4-ylcarbamoyl)butoxy)phenyl)methyl)carbamate (28),
2-(3-carbamimidoylphenoxy)pentanoic acid (2'-methoxybiphenyl-4-yl)amide (29),
2-[3-(N-hydroxycarbamimidoyl)phenoxy]pentanoic acid (2'-methanesulfonylbiphenyl-4-yl)amide (30),
2-(3-carbamimidoylphenoxy)pentanoic acid (2'-trifluoromethylbiphenyl-4-yl)amide (31).
ethyl(1-imino-1-{3-[1-(2'-methansulfonylbiphenyl-4-ylcarbamoyl)-butoxy]phenyl}methyl)carbamate (32),
2-[3-(N-pentanoyloxycarbamimidoyl)phenoxy]pentanoic acid-(2'-methansulfonyl-biphenyl-4-yl)amide (33),
2-[3-(N-(2-methylpropionyloxy)carbamimidoyl)phenoxyl]pentanoic acid (2'-methansulfonylbiphenyl-4-yl)amide (34),
2-[3-(N-benzoyloxycarbamimidoyl)phenoxyl]pentanoic acid(2'-methansulfonylbiphenyl-4-yl)amide (35),
2-[3-(N-acetoxycarbamimidoyl)phenoxy]pentanoic acid(2'-methansulfonyl-biphenyl-4-yl)amide (36),
isobutyl(1-imino-1-{3-[1-(2'-methansulfonylbiphenyl-4-ylcarbamoyl)butoxy]phenyl}methyl)carbamate (37),
butyl(1-amino-1-{3-[1-(2'-methansulfonylbiphenyl-4-ylcarbamoyl)butoxy]phenyl}methyl)carbamate (38),
isopropyl(1-imino-1-{3-[1-(2'-methansulfonylbiphenyl-4-ylcarbamoyl)butoxy]phenyl }methyl)carbamate (39),
2[3-(N-methoxycarbaminidoyl)phenoxy]pentanoic acid(2'-methansulfonylbiphenyl-4-yl)amide (40),
(S)-2-[3-(N-hydroxycarbaminidoyl)phenoxy]pentanoic acid (2'-methansulfonylbiphenyl-4-yl)amide (41),
(R)-2-[3-(N-hydroxycarbaminidoyl)phenoxy]pentanoic acid(2'-methansulfonylbiphenyl-4-yl)amide (42),
methyl(1-imino-1-{3-[(S)-1-(2'-methansulfonylbiphenyl-4-ylcarbamoyl)butoxy]phenyl}methyl)carbamate (43),
2-(3-carbamimidoylphenoxy)pentanoic acid(2'-methansulfonylbiphenyl-2-ylmethyl)amide (44),
2-(3-carbamimidoylphenoxy)-N-(2'-methanesulfonylbiphenyl-2-ylmethyl)-2-phenylacetamide (45),
2-(3-carbamimidoylphenoxy)-4-methylpentanoic acid-(2'-methansulfonyl-biphenyl-2-ylmethyl)amide (46),
4-(3-carbamimidoylphenoxy)-N-(2'-methansulfonylbiphenyl-4-yl)butyramide (47),
2-(7-carbamimidoylnaphthalin-2-yloxy)-N-(2'-methansulfonylbiphenyl-4-yl)-2-phenylacetamide (48),
3-(3-carbamimidoylphenoxy)-N-(2'-methansulfonylbiphenyl-4-yl)propionamide (49),
2-(3-carbamimidoylphenyl)pentanoic acid(2'-methansulfonylbiphenyl-4-yl)amide (50),
4-(3-carbamimidoylphenyl)-N-(2'-methansulfonylbiphenyl-4-yl)butyramide (51),
3-[3-(N-hydroxycarbamimidoyl)phenyl]-N-(2-methansulfonylbiphenyl-4-yl)propionamide (52),
2-(3-carbamimidoylphenoxy)pentanoic acid(3-fluor-2'-methansulfonylbiphenyl-4-yl)amide (53).

3. A pharmaceutical composition comprising at least one compound according to claim 1 or one of its physiologically acceptable salts, and a pharmaceutically acceptable vehicle or excipient.

4. A method for treating thrombosis, myocardial infarct, arteriosclerosis, inflammation, apoplexy, angina pectoris, restenosis after angioplasty or intermittent claudication comprising administering to a patient in need thereof a pharmaceutical composition according to claim 3.

5. A process for preparing a pharmaceutical composition, comprising bringing together into a dose form a compound according to claim 1 and/or one of its physiologically acceptable salts at least one solid, liquid or semi-liquid vehicle or excipient.

6. A method for inhibiting coagulation factor Xa, comprising administering to a patient in need thereof a pharmaceutical composition according to claim 3.

7. A method for inhibiting coagulation factor VIIa, comprising administering to a patient in need thereof a pharmaceutical composition according to claim 3.

8. A method for treating thrombosis comprising administering to a patient in need thereof a pharmaceutical composition according to claim 3.

9. A pharmaceutical composition comprising at least one compound according to claim 2 or one of its physiologically acceptable salts, and a pharmaceutically acceptable vehicle or excipient.

10. A method for treating thrombosis, myocardial infarct, arteriosclerosis, inflammation, apoplexy, angina pectoris, restenosis after angioplasty or intermittent claudication comprising administering to a patient in need thereof a pharmaceutical composition according to claim 9.

11. A method for inhibiting coagulation factor Xa, comprising administering to a patient in need thereof a pharmaceutical composition according to claim 9.

12. A method for inhibiting coagulation factor VIIa, comprising administering to a patient in need thereof a pharmaceutical composition according to claim 9.

13. A method for treating thrombosis comprising administering to a patient in need thereof a pharmaceutical composition according to claim 9.

14. A process for preparing a pharmaceutical composition, comprising bringing together into a dose form a compound according to claim 2 and/or one of its physiologically acceptable salts with at least one solid, liquid or semi-liquid vehicle or excipient.

15. A composition according to claim 1, wherein $R^1$ is phenyl substituted by —C(=NH)NH$_2$.

16. A composition according to claim 15, wherein —C(=NH)NH$_2$ is monosubstituted by —COOA, —OCOA, —CO[C(R$^7$)$_2$]$_n$-Ar', —OA, or —OH.

17. A composition according to claim 1, wherein $R^2$ is S(O)(O)A, —CF$_3$ or OA.

18. A composition according to claim 17, wherein $R^1$ is phenyl substituted by —C(=NH)NH$_2$.

19. A composition according to claim 15, wherein $R^2$ is S(O)(O)A.

* * * * *